US011439531B2

(12) United States Patent
Goel

(10) Patent No.: US 11,439,531 B2
(45) Date of Patent: Sep. 13, 2022

(54) ORTHOPEDIC SHOULDER BRACE

(71) Applicant: Danny Goel, Burnaby (CA)

(72) Inventor: Danny Goel, Burnaby (CA)

( * ) Notice: Subject to any disclaimer, the term of this patent is extended or adjusted under 35 U.S.C. 154(b) by 0 days.

(21) Appl. No.: 16/610,248

(22) PCT Filed: May 3, 2018

(86) PCT No.: PCT/CA2018/050531
§ 371 (c)(1),
(2) Date: Nov. 1, 2019

(87) PCT Pub. No.: WO2018/201255
PCT Pub. Date: Nov. 8, 2018

(65) Prior Publication Data
US 2021/0106453 A1 Apr. 15, 2021

Related U.S. Application Data

(60) Provisional application No. 62/554,804, filed on Sep. 6, 2017, provisional application No. 62/500,526, filed on May 3, 2017.

(51) Int. Cl.
*A61F 5/37* (2006.01)
*A63B 21/00* (2006.01)
*A61F 5/34* (2006.01)
*A61H 1/02* (2006.01)

(52) U.S. Cl.
CPC .............. *A61F 5/3738* (2013.01); *A61F 5/34* (2013.01); *A61F 5/3761* (2013.01); *A61H 1/0274* (2013.01); *A63B 21/154* (2013.01); *A63B 21/4017* (2015.10); *A61H 2201/1276* (2013.01);

(Continued)

(58) Field of Classification Search
CPC ........ A61F 5/3738; A61F 5/34; A61F 5/3761; A61F 5/3753; A61F 5/3792; A63B 21/4017; A63B 21/154; A63B 21/4013; A63B 2209/08; A63B 2209/10; A63B 2225/62; A63B 21/1609; A63B 21/0442; A63B 21/0552; A63B 23/03508; A63B 23/0494; A63B 23/1245; A61H 1/0274; A61H 2201/1276; A61H 2201/1635; A61H 2201/0126; A61H 2201/1638; A61H 99/00
See application file for complete search history.

(56) References Cited

U.S. PATENT DOCUMENTS 4,198,964 A * 4/1980 Honneffer ............. A61F 5/3738
602/19
4,753,240 A * 6/1988 Sparks ..................... A61F 7/02
602/14

(Continued)

*Primary Examiner* — Garrett K Atkinson

(57) ABSTRACT

An orthopedic brace for supporting a shoulder and an arm of a patient can comprise a sleeve, a pad, a pillow, and a system of adjustable straps for positioning and securing the sleeve in a desired position for treatment. The pad can comprise a plurality of pockets for accepting hot or cold compresses therein for providing thermal therapy, and can be removable from the brace to be used in isolation along other parts of the body. The adjustable straps can be replaced with tensile straps, and the sleeve can be positioned along different points of the patient's body to allow the patient to conduct various patient driven exercises, including patient driven range of motion or strengthening exercises.

17 Claims, 7 Drawing Sheets

(52) U.S. Cl.
CPC .. *A61H 2201/1635* (2013.01); *A63B 21/4013* (2015.10)

(56) References Cited

U.S. PATENT DOCUMENTS

| | | | | |
|---|---|---|---|---|
| 5,020,521 | A * | 6/1991 | Salort | A61F 5/0118 602/20 |
| 5,403,268 | A * | 4/1995 | Clement | A61F 5/3738 602/20 |
| 6,117,093 | A * | 9/2000 | Carlson | A63B 21/0056 482/44 |
| 6,477,448 | B1 * | 11/2002 | Maruyama | B25J 13/02 318/568.11 |
| 7,837,599 | B2 * | 11/2010 | Kowalczewski | A63B 23/12 482/904 |
| 8,221,049 | B1 * | 7/2012 | Westendorf | E02F 3/404 414/729 |
| 8,460,225 | B2 * | 6/2013 | Wickstrom | A61F 5/3738 602/4 |
| 8,636,630 | B2 * | 1/2014 | Morris | A63B 23/1209 482/117 |
| 8,834,169 | B2 * | 9/2014 | Reinkensmeyer | A61H 1/0274 D24/188 |
| 9,375,598 | B1 * | 6/2016 | Lai | A61H 1/0274 |
| 9,827,677 | B1 * | 11/2017 | Gilbertson | B25J 9/046 |
| 9,827,678 | B1 * | 11/2017 | Gilbertson | B25J 9/1682 |
| 10,201,901 | B2 * | 2/2019 | Sato | B25J 9/1674 |
| 10,384,096 | B1 * | 8/2019 | Aery | A63B 21/075 |
| 2003/0028130 | A1 * | 2/2003 | Wunderly | A61H 1/0274 482/4 |
| 2007/0265146 | A1 * | 11/2007 | Kowalczewski | G16H 40/63 482/142 |
| 2010/0160842 | A1 * | 6/2010 | Wickstrom | A61F 5/3738 602/4 |
| 2011/0155148 | A1 * | 6/2011 | Golden | A61F 7/00 128/878 |
| 2011/0287907 | A1 * | 11/2011 | Morris | A63B 21/00069 482/117 |
| 2012/0209159 | A1 * | 8/2012 | Fout | A61F 5/3738 602/4 |
| 2013/0226341 | A1 * | 8/2013 | Sturm | B25J 5/00 901/1 |
| 2014/0316308 | A1 * | 10/2014 | Lee | A63B 23/03508 601/33 |
| 2015/0360069 | A1 * | 12/2015 | Marti | A63B 23/1272 482/7 |
| 2018/0214740 | A1 * | 8/2018 | Horen | A63B 21/00069 |

* cited by examiner

ORTHOPEDIC SHOULDER BRACE

FIELD

Embodiments of the invention generally relate to an orthopedic device for supporting a shoulder and an arm of a patient. More particularly, embodiments of the invention relate to a shoulder brace that promotes mobility and can be adapted to be used for patient driven exercises, such as strengthening exercises and range of motion exercises, for multiple parts of the body. These exercises may be instructed to the patient via an application (phone app) or via head mounted display in virtual reality or augmented reality.

BACKGROUND

The human shoulder is made up of three bones: the clavicle (collarbone), the scapula (shoulder blade), and the humerus (upper arm bone) as well as associated muscles, ligaments and tendons. The articulations between the bones of the shoulder make up the shoulder joint. The shoulder joint, also known as the glenohumeral joint, is the major joint of the shoulder. It is a ball and socket joint, formed by the humerus and scapula and their surrounding structures, such as ligaments, muscles, tendons, which support the bones and maintain the relationship of one to another. The shoulder joint allows the arm to rotate in a circular fashion, to hinge away from the body, and is capable of rotation within multiple planes when the arm is displaced relative to the torso.

The shoulder must be mobile enough for a wide range of actions of the arms and hands, but also stable enough to allow for actions such as lifting, pushing and pulling. As the human shoulder can be unstable, it can be easily injured. Common problems include but are not limited to: sprains and strains, dislocations, separations, tendinitis, bursitis, torn rotator cuffs, frozen shoulder, fractures, and arthritis.

Treatment of shoulder injuries frequently require determining a desired optimal treatment position of the shoulder and associated arm, and then placing the shoulder and arm in the desired treatment position. Such recuperative treatments are particularly applicable to soft tissue injuries involving damage to one or more connective shoulder ligaments, and is often the treatment of choice following a number of surgical procedures, such as recurrent anterior subluxation surgery, rotator cuff surgery, humeral head replacement or fracture fixation, and similar.

Support devices for the shoulder, such as orthopedic braces, rigid casts, and slings are commonly used to perform the placement and immobilization of the shoulder and arm in the desired treatment position following or in the absence of surgery.

SUMMARY

Embodiments of an orthopedic device of the present invention can comprise a sleeve, a pad, and adjustable straps. For the purposes of this disclosure, orthopedic means surgical or non-surgical procedures relating to functional impairment of the skeletal system and associated structures, including but not limited to tendons, ligaments, bones, muscles and joints.

In an embodiment, the orthopedic device or brace comprises a sleeve for supporting a portion of a patient's arm, a pad for supporting a portion of the patient's shoulder, and adjustable straps for permitting the patient to adjust and secure the position of the sleeve and the shoulder pad which is meant for thermal therapy.

In another embodiment, the shoulder pad can be removable from the brace and can be used in isolation for another portion of the body for thermal therapy.

In another embodiment, the adjustable straps can be tensile straps for permitting patient driven exercises as part of the patient's rehabilitation program.

In another embodiment, the sleeve can be removed from the brace and be used in isolation with tensile straps for patient driven exercises.

DETAILED DESCRIPTION

Figure 1:
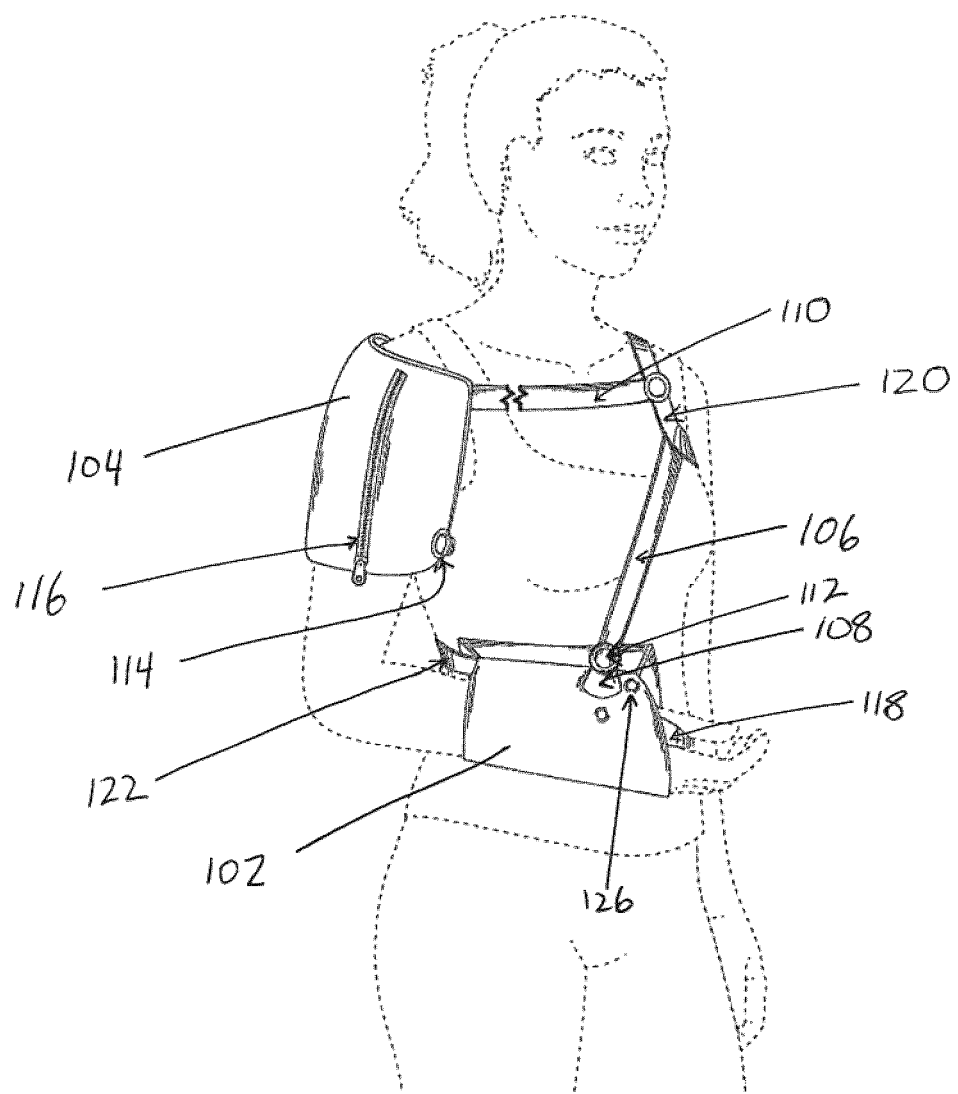
FIG. 1 is a front perspective view of an embodiment of the present invention, illustrating an orthopedic shoulder brace having a sleeve for supporting a portion of a patient's arm, a wedge shaped pillow and a shoulder pad for supporting and providing therapeutic benefit to a portion of the patient's shoulder, and adjustable straps for positioning and securing the sleeve and/or shoulder pad.

With reference to FIG. 1, an embodiment of an orthopedic shoulder brace 100 comprises a sleeve 102 and a shoulder pad 104, and a system of adjustable straps, namely a primary supporting strap 106, for supporting the securing portions of the patient's body in desired positions for treatment. In embodiments, the adjustable straps can also include attachments such as an optional contra-lateral shoulder strap 120.

Operatively, and in an embodiment, the sleeve 102 can be used to support a patient's arm in a desired position by using a primary supporting strap 106. As shown, the primary supporting strap 106 can be removably attached to a distal end of the sleeve 102 and can be extend along and across a front of the patient's torso towards the patient's opposite shoulder. Thereabout, the primary supporting strap 106 can be connected to an optional contra-lateral shoulder strap 120. Although not shown, in an embodiment, the primary supporting strap 106 can go around the patient's opposite shoulder and extend back towards the distal end of the sleeve 102 to connect thereto. As shown in FIG. 1, the primary supporting strap 106 is in tension, thereby supporting the sleeve 102 and keeping the sleeve 102 in a stable (generally constant but not rigidly fixed) position with respect to the shoulder (shown proximal to the optional contra-lateral shoulder strap 120) of the patient.

Applicant notes that the sleeve 102 is of a sufficient length to ensure that it does not interfere with the movement of the patient's elbow. Accordingly, and as shown, the sleeve 102 is shorter than a length of the patient's lower arm. Absent any interference with the movement of the patient's elbow, the patient is provided with greater freedom of movement of the elbow for increased comfort and mobility. As a further advantage, the freedom of movement of the elbow permits a patient to use the orthopedic shoulder brace 100 for a variety of patient driven exercises for rehabilitation and/or for muscle strengthening exercises.

To assist in spacing the patient's arm away from the patient's torso (if required) and to assist in securing the patient's arm in a desired position, the sleeve 102 can be adapted to support a supportive pad such as a wedge shaped pillow 112 between the patient's arm and the patient's torso. In embodiments, more than one wedge shaped pillow can be positioned between the sleeve 102 and the patient's torso. In another embodiment, the wedge shaped pillow can be made from a suitable material, such as a foam material. Further still, in other embodiments, the wedge shaped pillow 112 can be custom shaped to have a contour that fits the patient's body shape.

The wedge shaped pillow 112 may or may not be attached via strap but may be removably attached to the sleeve 102. This attachment may be by any combination of fasteners including hook and loop fasteners (e.g., Velcro) or magnets, which permits ease of removal by the patient. It may also serve to increase or decrease the degree of external rotation to accommodate the position of the shoulder following surgery or in the absence of surgery but following a particular diagnosis. This may be accommodated by increasing or decreasing the number of wedge shaped pillows based on size of the patient (see below for patient customization). In addition, wedge shaped pillow 112 may also contain partially or in whole, inflatable portions that may provide comfort for the user during periods of prolonged rest or sleep. This portion may be inflated using both mechanical and non-mechanical means. The wedge shaped pillow 112 can also consist of a storage compartment, such as a pocket, where medications and other non-valuable items may be stored by the patient during the early phases following or in the absence of surgery.

Figure 2:
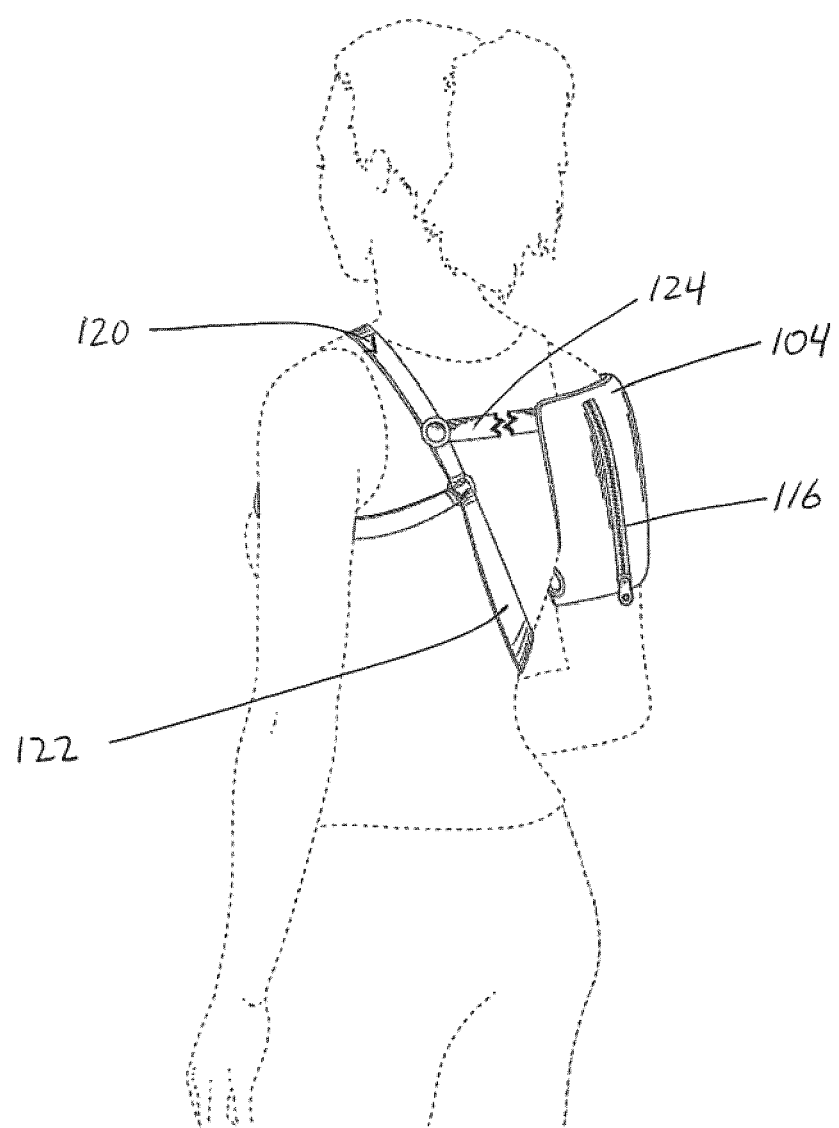
FIG. 2 is rear perspective view of the embodiment as shown in FIG. 1.

The sleeve 102 can be maintained at a desired position adjacent the patient's torso through a system of adjustable straps. The primary supporting strap 106 can be removably secured to the sleeve 102 via an attachment means 108 at a distal end thereof. The primary supporting strap 106 extends from a distal end of the sleeve 102, along a front of the patient's torso and can be secured to an optional contra-lateral shoulder strap 120. As shown in FIGS. 1 and 2, the contra-lateral shoulder strap 120 can be secured around the patient's shoulder, opposite to the patient's shoulder requiring the assistance of the orthopedic shoulder brace 100. Straps may be secured to one another or to the sleeve 102 or the shoulder pad 104 by any form of fastener, including but not limited to a stitch, a hook and ring, a hook and loop, a hasp, a clasp, a snap, a button, magnetic device, or any combination of fasteners. The fastener may be in a fixed position or may be adjustable, for example, by sliding along a strap. A fastener may be substantially permanent (not readily detachable) or readily detachable.

As discussed previously in embodiments, the primary supporting strap 106 can extend along a front of the patient's torso, towards the patient's opposite shoulder and connect with an optional contra-lateral strap 120. In embodiments, and as shown in FIGS. 1 and 2, the contra-lateral strap 120 can extend around the patient's opposite shoulder, and extend along a back of the patient's torso to operatively connect with an extension strap 122 at about a mid-point of the patient's back. The extension strap 122 can extend from a proximal end of the sleeve 102, along the patient's torso and up along the patient's back. Applicant notes that for the purposes of this application, proximal and proximate can be used interchangeably and are synonymous with one another.

In an embodiment, the extension strap 122 can be removable and be detachable from the sleeve 102 and contra-lateral shoulder strap 120. In a variation, the primary supporting strap 106 and extension strap 122 may comprise a unitary structure extending over the shoulder and along the patient's back, and the shoulder strap 120 may be attached to this unitary structure at the front of the patient's torso, and extend proximal to the patient's armpit to the back, where is may be attached to the unitary structure again. Straps that are connected to one another may be physically joined, in a permanent or removable fashion, and may be connected by one or more intermediate elements, such as a connecting ring or other fastener. In a further variation, other straps may be part of a unitary structure. Even if constructed as a unitary structure, it may be possible to speak of different parts of the strap, such as the primary supporting strap or the sternum strap or the contra-lateral strap. There are many other strap configurations that are possible, and the concept is not restricted to only those particular configurations that are shown or explicitly described.

In embodiments, the shoulder pad 104 can be removable to permit washing thereof for increasing longevity, and comprises of at least one storage compartment, such as an internal pocket 116 for accepting removable hot or cold compresses therein—including but not limited to iced water, ice, gel or other product—for thermal therapy. In an embodiment, and as shown in FIG. 2, the shoulder pad 104 can have a plurality of internal pockets or storage compartments. As shown, the internal pocket 116 can further comprise a zipper for securing any items placed therein.

In an embodiment, the shoulder pad 104 can be positioned around the patient's biceps by adjustable straps 110, 114. In FIGS. 1 and 2, adjustable strap 114 is largely concealed by the shoulder pad 104 and the arm of the patient. In an embodiment, and as shown in FIG. 1, adjustable strap 110 can be a two-part strap, with a first portion being used as a sternum strap for removably securing the shoulder pad to the contra-lateral strap 120, and a second portion being used as an anterior lateral strap 124 to removably secure the pad 104 to the contra-lateral strap 120. In some variations, the sternum strap 110 may be secured to the supporting strap 106. The sternum strap 110 can be positioned along a front of the patient's torso, as shown in FIG. 1, while the anterior lateral strap 124 can be positioned along a back of the patient, as shown in FIG. 2. As shown, the sternum strap 110 interconnects the shoulder pad 104 with the contra-lateral shoulder strap 120, and the anterior lateral strap 124 interconnects the shoulder pad 104 with the contra-lateral shoulder strap 120. As shown in FIG. 1, the sternum strap 110 is in tension, thereby helping hold the shoulder pad 104 in a stable position with respect to the shoulder (shown proximal to the shoulder pad 104) of the patient. In embodiments, both the sternum strap 110 and the anterior lateral strap 124 are removable and/or detachable from both the shoulder pad 104 and the contra-lateral shoulder strap 120.

Figure 3:
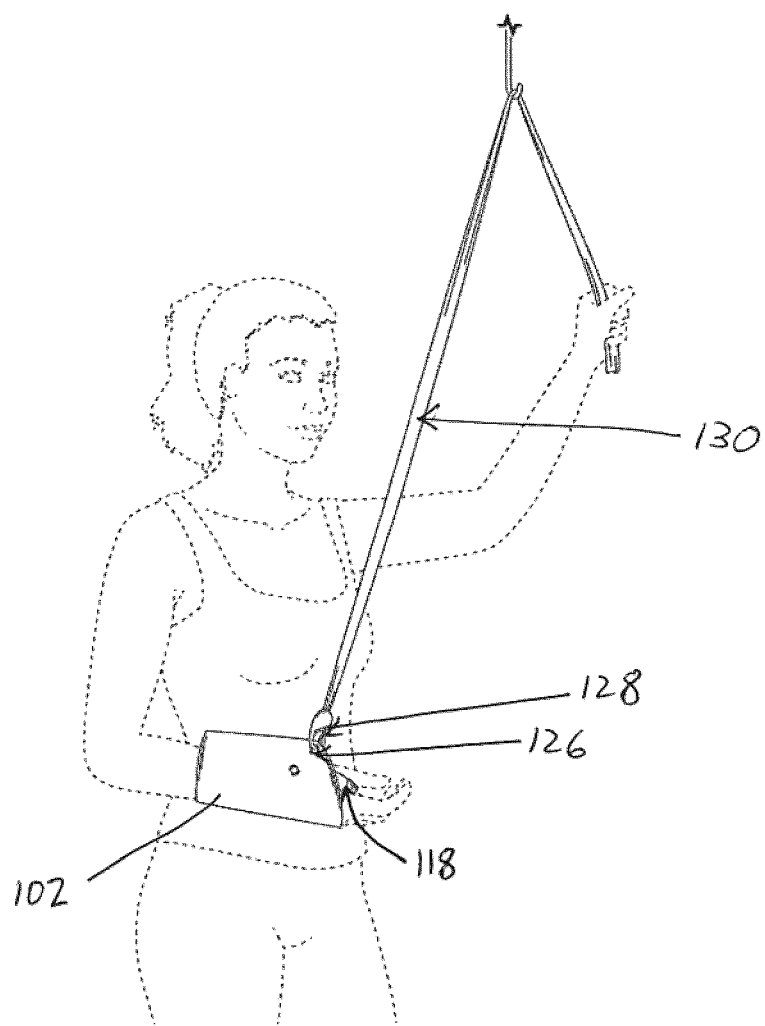
FIG. 3 is a front perspective view of an embodiment of the present invention, illustrating a strap attached to a sleeve of the orthopedic shoulder brace for permitting patient driven range of motion exercises.

In reference to FIG. 3, the orthopedic shoulder brace 100 can be adapted and be used for a multitude of patient driven exercises, including patient driven range of motion (ROM) exercises. To adapt the orthopedic shoulder brace 100 for use as part of patient driven ROM exercises, the system of adjustable straps for positioning and securing the sleeve 102 can be removed and replaced with a single ROM exercise strap 130. As shown, a proximal end 128 of the ROM exercise strap 130 can be removably interconnected with the sleeve 102 at the distal end thereof using an attachment means 126. The attachments means 126 can include a hook or other fastener or means at the proximal end 128 of the ROM strap 130 for securing to a grommet at the distal end of the sleeve 102.

As shown in FIG. 3, the ROM exercise strap 130 can have a handle at a distal end thereof and be adapted to interconnect with a hook or pulley secured to a wall to act as a fulcrum.

Figure 4:
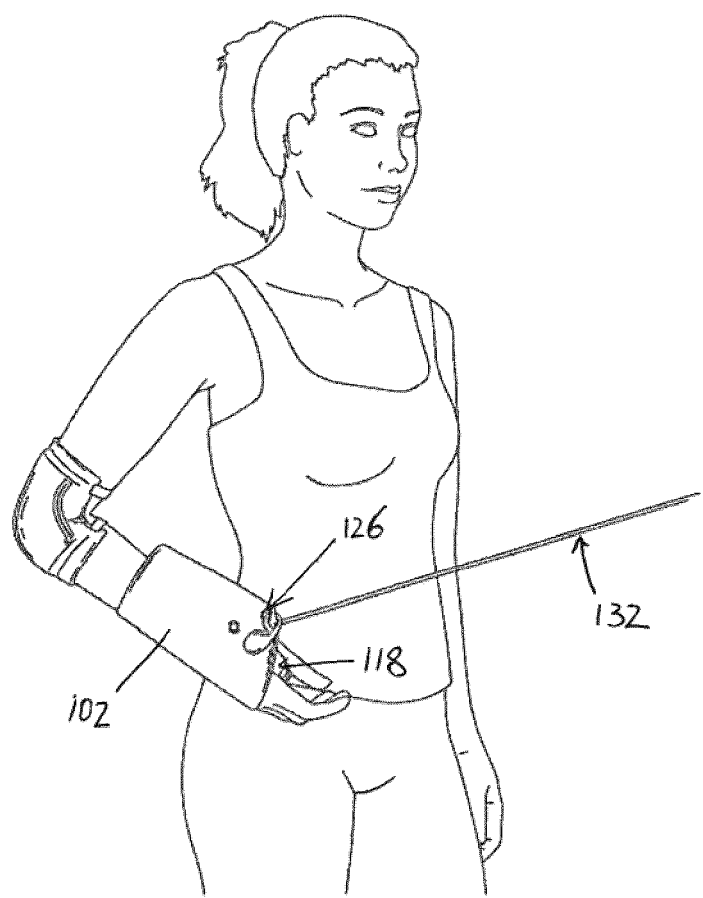
FIG. 4 is a front perspective view of an embodiment of the present invention, illustrating a tensile band or strap attached to a sleeve of the orthopedic shoulder brace for permitting patient driven strengthening exercises.

With reference to FIG. 4, in another embodiment, the orthopedic shoulder brace 100 can be used for patient driven strengthening exercises for the patient's elbow. As shown, a proximal end of a tensile strap 132 can be removably secured to the sleeve 102 at the distal end thereof, using a similar attachment means as shown in FIG. 3. The distal end (not shown) of the tensile strap 132 can be removable secured to an attachment point on a rigid surface. As discussed above, the length of the sleeve 102, being shorter than the length of the patient's lower arm provides freedom of movement of the patient's elbow to allow such strengthening exercises.

Figure 5:
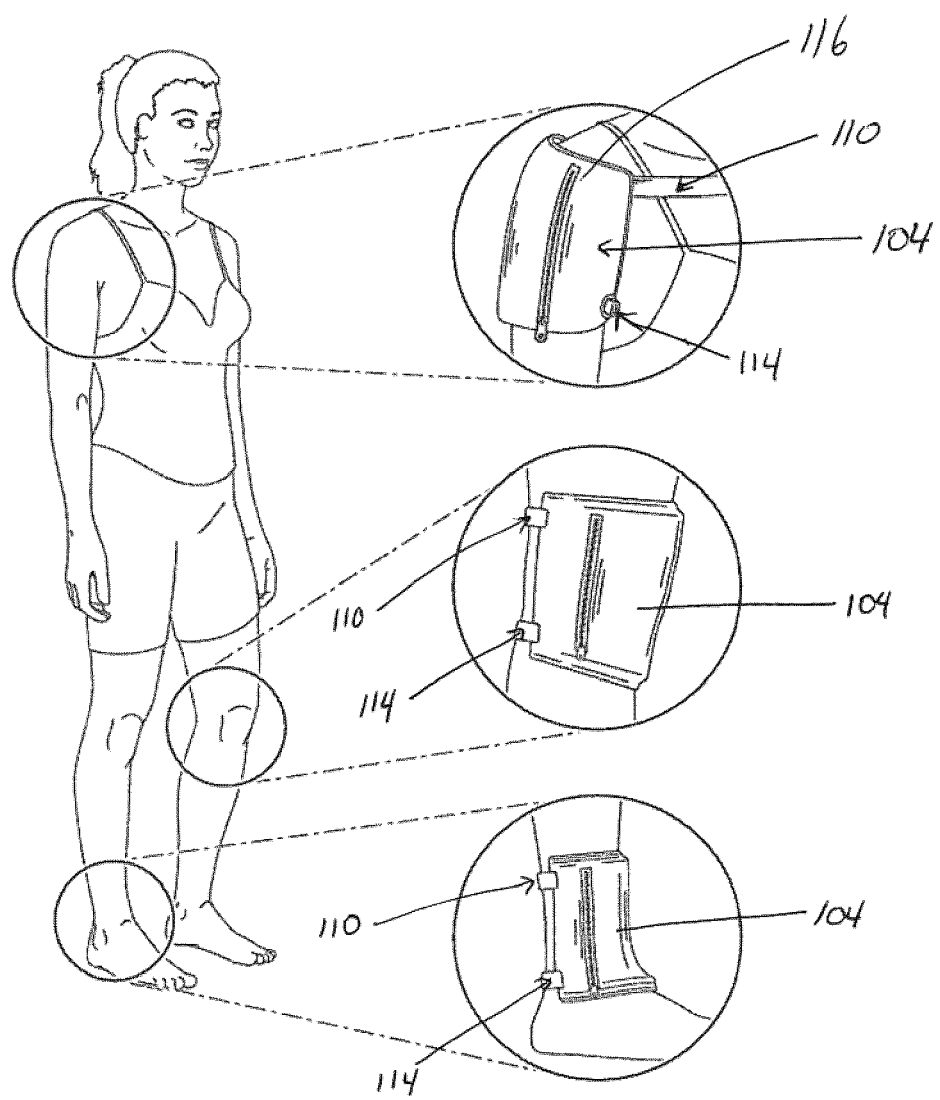
FIG. 5 is a perspective view of an embodiment of the present invention illustrating the shoulder pad of the orthopedic shoulder brace being used as a cold therapy pad on other portions of the body.

As shown in FIG. 5, in an embodiment, the shoulder pad 104 can be adapted and be used for localized thermal therapy. As shown, the adjustable strap 110 can be removed from the contra-lateral strap 120 to disconnect the shoulder pad 104 from the orthopedic shoulder brace 100, allowing the shoulder pad 104 to be positioned about any other point on the patient's body, such as a knee or ankle. Adjustable straps 110 and 114 can be used to secure the shoulder pad 104 about the patient (e.g., about the knee and/or ankle, or any other joint of the body). As discussed previously, the shoulder pad 104 can comprise a plurality of pockets for accepting hot or cold compresses for thermal therapy.

Figure 6:
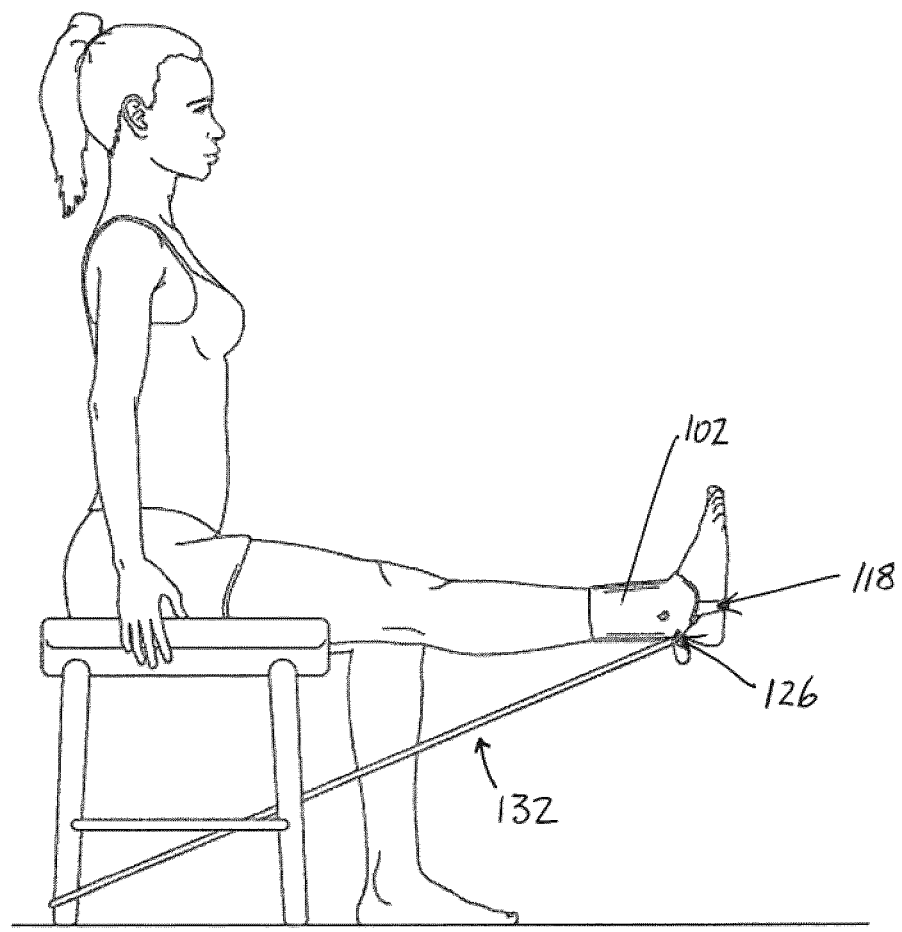
FIG. 6 is a perspective view of an embodiment of the present invention, illustrating patient driven strengthening exercises for other or all parts of the body, including knee resistive exercises.

As shown in FIG. 6, in an embodiment, the distal end of the tensile strap 132 can be secured to any stable supporting structure, such as a chair on which the patient sits on, and the sleeve 102 can be positioned and secured about the patient's ankle. An adjustable retention strap 118 can provide additional support in securing the sleeve 102 about the ankle. The patient can then use the orthopedic shoulder brace 100 to conduct patient driven strengthening exercises of the patient's knee. Similar apparatus may be used for all other joints of the body; generally the straps are arranged to accommodate a particular joint.

Figure 7:
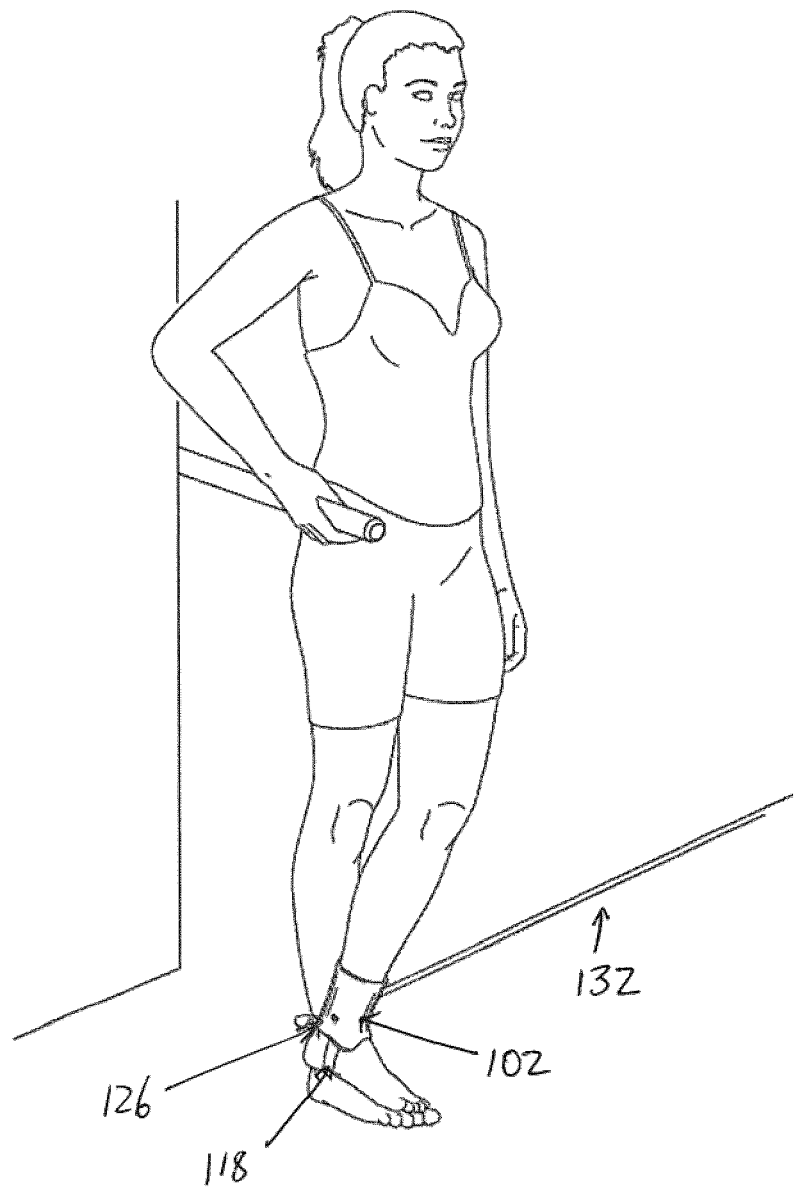
FIG. 7 is a perspective view of an embodiment of the present invention, illustrating patient driven strengthening exercises for any or all other parts of the body, including adductor exercises.

As shown in FIG. 7, in another embodiment, the distal end of the tensile strap 132 can be secured to a rigid structure (not shown) and the sleeve 102 secured to patient's ankle. With the patient standing upright, lateral movement of the leg on which the sleeve 102 is secured, allows the patient to conduct patient driven strengthening exercises, such as hip adductor exercises.

The devices described herein can be constructed from any number of materials or combinations of materials. Materials may be selected based upon considerations such as strength (including strength in compression and tension), function, comfort, washability, olfactory effects (such as whether the materials tend to acquire an unpleasant odour from normal use), aesthetics, durability, cleanliness, ease of sizing, adjustability, moisture-handling, breathability (admitting air passage and/or enabling evaporation), allergenic qualities, antibacterial/antimicrobial qualities, environmental renewability/friendliness, and economics. Rigid (and some semi-rigid) structures may be made from any material or combination of materials, such as (but not limited to) plastics, metals, ceramics, silicones, synthetic materials such as molded carbon fibres, organic materials such as bamboo or wood, and various composites. Soft or flexible or elastic or cloth-like structures may be made from any material or combination of materials, such as (but not limited to) plastics, metals (e.g., chains), silicones, cloth, natural or synthetic rubber, synthetic materials such as nylon, natural materials such as cotton, and various composites. Some materials may be made in different forms that exhibit different physical properties; for example, some polymers can be made more rigid or more flexible by controlling synthesis of cross-linkages.

The following materials are examples of materials that may be used, individually or in concert with other materials, to apply the concepts described herein: bamboo, cotton, Gore-Tex® (polytetrafluoroethylene (PTFE), including stretched PTFE or expanded PTFE (ePTFE)), nylon, polyester, polypropylene, Spandex (elastane or Lycra; also known by other names); rayon fibres such as Tencel® (Lyocell), wool, and X-Static® (metal bonded to polymer). Various properties of these materials are well-known.

As previously indicated, the devices are sized and shaped to be used with a human body. Some devices include adjustable elements that enable the devices to be sized and shaped to be secured to a part of a human body (such as an arm and/or the knee and/or ankle), and to be sized and shaped to be used with other device elements in different places on a human body. For example, the devices can be sized and shaped to adapt to patients having a range of chest measurements, or arm lengths, or body sizes. In another variation, the devices can be patient-specific, that is, custom made or fitted for a particular patient. In a further variation, some components (such as straps) may be sized and shaped and adjusted for patients of variant sizes and shapes, while other components (such as the sleeve 102) may be patient-specific.

Components that are patient-specific may be constructed in any fashion. Some types of rigid or semi-rigid components may be constructed by a computer-controlled process such as 3D printing or computer-controlled molding. Some soft or flexible or elastic or cloth-like structures may also be produced by a computer-controlled process for a customized fit. Patient-specific images or patient-specific measurements or patient-specific molding may serve as inputs to the computer-controlled process, which generates the patient-specific component as a function of the patient-specific inputs. A patient-specific sleeve 102, for example, may advantageously accommodate the size and shape of the arm of a particular patient, as well as the injury of the particular patient, as well as the build of the patient (such as the presence of muscle or fat), and any medical further considerations of the particular patient (such as the presence of a cast or brace or sensitive area or bandage or surgical closure such as stitches). Patient-specific images or other input data may come from penetrative medical scans (such as X-rays or ultrasound), or non-penetrative scans (such as external optical photography), or other medical scans or measurements, or any combination thereof.

In the case of the sleeve 102, the sleeve 102 may be sized and shaped to support the arm of the patient and also sized and shaped to be shorter than the length of the lower arm of the patient such that the sleeve 102 is short of the elbow of the patient and does not interfere with the movement of the patient's elbow. Similarly, as shown in FIGS. 1 and 2, the pad 104 may be sized and shaped to be shorter than the length of the upper arm of the patient such that the pad 104 (when secured proximal to the shoulder of the patient) does not interfere with the movement of the patient's elbow. As depicted in FIG. 1, the sleeve 102 and the pad 104 may be sized and shaped so that, in ordinary usage, the sleeve 102 and the pad 104 do not contact one another.

The straps may be sized and shaped to support the sleeve 102 by tension. The straps may be sized and shaped to be in tension, and support the pad 104 and/or hold the pad in position on the upper arm of the patient.

The concepts described herein may realize one or more advantages, some of which have been mentioned already. The concepts support customization of devices (or parts thereof) for specific patients, which may assist with patient recovery by, for example, improving patient comfort during day-to-day activities, as well as offering patient comfort during activities such as patient driven exercises or sleep. Use of a computer-controlled process may make customization a viable option that is readily available to many patients.

The embodiments described above and shown in the drawings are intended to be examples only. Alterations, modifications and variations can be effected to the particular embodiments without departing from the scope of the concept, which is defined by the claims appended hereto.

Referring back to FIGS. 3 to 6, instructions on how a patient may conduct the various patient driven exercises, including patient driven range of motion exercises can be provided to the patient using known methods, including but not limited to personal instruction, cellular or mobile phone application, or through virtual or augmented reality.

The invention claimed is:

1. An orthopedic brace for providing support to an arm and a shoulder on a same side of a body of a user of the orthopedic brace as the arm, the brace comprising:
   a sleeve for supporting the arm, the sleeve having a proximal end and an opposite distal end;
   a shoulder pad for supporting the shoulder; and
   adjustable straps for removably securing the shoulder pad to the sleeve and positioning the shoulder pad and sleeve in a desired position relative to the arm and shoulder, wherein the adjustable straps further comprise:
      an adjustable primary strap having a proximal end removably attached to the proximal end of the sleeve, and a distal end removably attached to the distal end of the sleeve; and
      a removable and adjustable contra-lateral strap for removably securing the shoulder pad to the primary strap.

2. The orthopedic brace of claim 1, further comprising a supportive pad for positioning the sleeve apart from the body of the user of the orthopedic brace.

3. The orthopedic brace of claim 2, wherein the supportive pad comprises a foam material.

4. The orthopedic brace of claim 2, wherein the supportive pad is contoured to fit a body shape of the user.

5. The orthopedic brace of claim 2, wherein the supportive pad has a wedge-shaped cross-sectional profile.

6. The orthopedic brace of claim 2, wherein the supportive pad comprises two or more supportive pads.

7. The orthopedic brace of claim 2, wherein the supportive pad is removably secured to the sleeve.

8. The orthopedic brace of claim 2, wherein the supportive pad comprises one or more inflatable portions for increasing a comfort level of the user.

9. The orthopedic brace of claim 2, wherein the supportive pad further comprises a storage compartment.

10. The orthopedic brace of claim 1, wherein the shoulder pad further comprises a storage compartment.

11. The orthopedic brace of claim 10, wherein the storage compartment further comprises a zipper to open and close the storage compartment.

12. The orthopedic brace of claim 1, wherein the shoulder pad comprises a removable shoulder pad.

13. The orthopedic brace of claim 1, wherein the sleeve is configured to have a length that is less than a length of the arm to allow freedom of movement of an elbow.

14. The orthopedic brace of claim 13, wherein the supportive pad is configured to have a length that is less than the length of the sleeve.

15. The orthopedic brace of claim 1, wherein the adjustable straps further comprise a removable and adjustable extension strap.

16. The orthopedic brace of claim 1, wherein the adjustable straps further comprise a removable and adjustable retention strap.

17. A method of conducting patient driven exercises, the method comprising:
   providing an orthopedic brace, the orthopedic brace comprising:
      a sleeve for supporting an arm, the sleeve having a proximal end and an opposite distal end;
      a shoulder pad for supporting a shoulder on a same side of a body of a user of the orthopedic brace as the arm; and
      adjustable straps for removably securing the shoulder pad to the sleeve, and positioning the shoulder pad and sleeve in a desired position relative to the arm and shoulder, wherein the adjustable straps further comprise:
         an adjustable primary strap having a proximal end removably attached to the proximal end of the sleeve, and a distal end removably attached to the distal end of the sleeve; and
         a removable and adjustable contra-lateral strap for removably securing the shoulder pad to the primary strap;
   providing a range of motion exercise strap; and
   providing instructions respecting the patient driven exercises, the instructions provided via one or more of personal instruction, cellular or mobile phone application, virtual reality instruction, and/or augmented reality instruction.

* * * * *